United States Patent [19]
Canfield et al.

[11] Patent Number: 5,610,710
[45] Date of Patent: Mar. 11, 1997

[54] DUAL MODE ILLUMINATION SYSTEM FOR OPTICAL INSPECTION

[75] Inventors: Donald H. Canfield, Vestal; Todd C. Fellows, Endicott; Earle W. Gillis; Peter J. Yablonsky, both of Apalachin, all of N.Y.

[73] Assignee: International Business Machines Corporation, Armonk, N.Y.

[21] Appl. No.: 654,513

[22] Filed: May 28, 1996

[51] Int. Cl.⁶ .................................................. G01N 21/00
[52] U.S. Cl. ........................ 356/237; 356/384; 356/136; 356/378
[58] Field of Search ................................. 356/237, 136, 356/384, 378, 128

[56] References Cited

U.S. PATENT DOCUMENTS

| | | | |
|---|---|---|---|
| 3,643,101 | 2/1972 | Shipp et al. | 356/384 |
| 3,806,252 | 4/1974 | Harris et al. | 356/384 |
| 4,527,870 | 7/1985 | Esmay | 350/523 |
| 4,871,257 | 10/1989 | Suzuki et al. | 356/400 |
| 4,878,736 | 11/1989 | Hekker et al. | 350/162.13 |
| 4,949,172 | 8/1990 | Hunt et al. | 358/101 |
| 5,008,743 | 4/1991 | Katzir et al. | 358/101 |
| 5,122,737 | 6/1992 | Clauberg | 324/158 |
| 5,185,638 | 2/1993 | Conzola et al. | 356/237 |
| 5,197,105 | 3/1993 | Uemura et al. | 382/8 |
| 5,216,479 | 6/1993 | Dotan et al. | 356/73 |
| 5,216,485 | 6/1993 | Bird et al. | 356/394 |
| 5,268,735 | 12/1993 | Hayashi | 356/237 |
| 5,288,991 | 2/1994 | King et al. | 250/216 |
| 5,301,012 | 4/1994 | King et al. | 356/398 |
| 5,353,112 | 10/1994 | Smith | 356/244 |
| 5,359,416 | 10/1994 | Mueller | 356/371 |
| 5,432,600 | 7/1995 | Grollimund et al. | 356/237 |

FOREIGN PATENT DOCUMENTS

| | | |
|---|---|---|
| 01195349 | 8/1989 | Japan . |
| 0634345 | 2/1994 | Japan . |
| 0627028 | 2/1994 | Japan . |

OTHER PUBLICATIONS

"Optical Inspection of Hole Bottoms," *IBM Technical Disclosure Bulletin*, May 1982, p. 6280.

"Optical Inspection System," *IBM Technical Disclosure Bulletin*, Feb. 1981, pp. 4076–4077.

"Dimensional Measurement of moving holes using spatial filtering," Suemoto, Y., Automatic Optical Inspection Conference, Innsbruck, Austria, 15–18 Apr. 1986, Fac. of Eng., Kagoshima Univ., Japan; SPIE; SIRA, vol. 654, pp. 166–172, 1986.

"An automatic in–line optical defect inspection system for aperture grilles," Chiu, C. and Orband, D., Optical Pattern Recognition V, Orlando, FL, USA, 5–6 Apr. 1994, Dept. of R&D, Sony Electron Inc., Orangeburg, NY, USA; *Proc. SPIE–Int. Soc. Opt. Eng. (USA)*, vol. 2237, pp. 234–250, 1994.

"Miniaturized micro–optical scanners," Motamedi, M. E., et al., Rockwell Sci. Center, Thousand Oaks, CA, USA, *Opt. Eng.*, Bellingham (USA), vol. 33, No. 11, pp. 3616–3623, Nov. 1994.

(List continued on next page.)

*Primary Examiner*—Georgia Y. Epps
*Assistant Examiner*—Reginald A. Ratliff
*Attorney, Agent, or Firm*—Jenkens & Gilchrist

[57] ABSTRACT

A dual mode illumination system for optical inspection of products for surface defects and defects in holes in the product includes a first light source for providing illumination along an axis of one or more holes in the product to be inspected, the first light source being positioned on a first side of the product, a second light source providing illumination of the surface of the second side of the product to be inspected, a beam splitter for redirecting light from the second light source to a light sensor while passing light from the first light source to the light sensor. The second light source may be located adjacent to a second side of the product to be tested with the axis of illumination parallel to a major plane of the product. The light sensor may be a video camera connected to a data processing and display system.

12 Claims, 4 Drawing Sheets

OTHER PUBLICATIONS

"Die-to-die inspection of phase-shifting masks," Stolpe, D. J., et al, 13th Annual Symposium on Photomask Technology and Management, Santa Clara, CA, USA, 22–23 Sep. 1993; *Proc. SPIE–Int. Soc. Opt. Eng. (USA)*, vol. 2087, pp. 200–215, 1994.

"Minimising optical overlay measurement errors," Smith, N., et al., Integrated Circuit Metrology, Inspection, and Process Control VII, San Jose, CA, USA, 2–4 Mar. 1993; *Proc. SPIE–Int. Soc. Opt. Eng.* (USA), vol. 1926, pp. 450–462, 1993.

"Determining the optimum image recording conditions in shearography based on spatial frequency considerations," Chau, F. S. and Ng, T.W., Industrial Applications of Optical Inspection, Metrology and Sensing, Boston, MA, USA, 19–20 Nov. 1992; *Proc. SPIE–Int. Soc. Opt. Eng.* (USA), vol. 1821, pp. 15–26, 1993.

"A measurement system for the visual analysis of integrated micromechanical devices," de Graaf, G., et al., EUROSENSORS VI, San Sebastian, Spain, 5–7 Oct. 1992; *Sens. Actuators A, Phys.* (Switzerland), vol. A37–A38, pp. 772–778, Jun.–Aug. 1993.

"Extraction features from images using video feedback," Boone, B. G., et al., Automatic Object Recognition, Orlando, FL, USA, 3–5 Apr. 1991; *Proc. SPIE–Int. Soc. Opt. Eng.* (USA), vol. 1471, pp. 390–403, 1991.

"Tile inspection—the right applications," Coulthard, M., *Sens. Rev.* (UK), vol. 11, No. 2, pp. 15–18, 1991.

"Microscopic objectives for semiconductor technology," Vollrath, W., Optical Microlithography and Metrology for Microcircuit Fabrication, Paris, France, 27–28 Apr. 1989; *Proc. SPIE–Int. Soc. Opt. Eng.* (USA), vol. 1138, pp. 166–171, 1989.

"Optical monitor of the defocused resist (VLSI photolithography)," Ikubo, H., et al., Proceedings of the Third Symposium on Automated Integrated Circuits Manufacturing, Honolulu, HI, USA, 18–23 Oct. 1987; Electrochem. Soc., viii+484, pp. 229–238, 1988.

"Dimensional measurement of moving holes using spatial filtering," Suemoto, Y., Automatic Optical Inspection, Innsbruck, Austria, 15–18 Apr. 1986; *Fac. of Eng.*, Kagoshima Univ., Japan; SPIE; SIRA, vol. 654, pp. 166–172, 1986.

"Limitation of optical inspection," Awamura, D., SEMI Technology Symposium 84. Technical Program Proceedings, Tokyo, Japan, 7–8 Dec. 1984; NJS Corp., Yokohama, Japan; *Semicond. Equipment & Mater Inst.*, Mountain View, CA, USA, 308, pp. 17/45, 1984.

"Optical figure inspection of diamond-timed metal mirrors," Shagam, R. N., et al., *Opt. Eng.* (USA), vol. 16, No. 4, pp. 375–380, Jul.–Aug. 1977.

U.S. patent application Ser. No. 08/117,582 filed Sep. 2, 1993.

DUAL MODE ILLUMINATION SYSTEM FOR OPTICAL INSPECTION

BACKGROUND OF THE INVENTION

1. Field of the Invention

The present invention relates to an automated optical inspection system and, more particularly, to an automated optical inspection system employing a combination of reflective and thru-lighting means for detecting defects in work pieces having one or more apertures, such as printed circuit boards or cathode ray tube shadow masks.

2. Prior Art

There are many optical inspection systems available in the prior art. Illumination configurations for inspection are typically applied in either of two configurations. A reflective illumination configuration provides for inspection of surface features and planes, while a "backlight" or "thru-light" configuration provides for inspection of holes in a mask or printed circuit board such as drilled or etched holes that go entirely through the product being inspected.

The following patents illustrate the prior art optical inspection systems:

U.S. Pat. No. 5,185,638 teaches a flexible and automated optical inspection system for printed circuit boards with illumination of surface features and multiple light sources to include the collection of light reflected from the surface.

The patent does not teach nor suggest an automated optical inspection system which provides simultaneous inspection of surface defects and drilled or etched holes in a product being inspected as it taught and claimed herein.

U.S. Pat. No. 5,197,105 teaches a method of reading an optical image of an inspected surface which employs multiple wavelength energy sources with multiple energy detection sensors specifically related to angular aperture applications.

The patent does not teach nor suggest an automated optical inspection system which provides simultaneous inspection of surface defects and drilled or etched holes in a product being inspected as it taught and claimed herein.

U.S. Pat. No. 5,216,479 discloses an optical inspection system with the imaging of an aperture in a reflecting surface and a first focal line co-planar with a first surface of a laminate. The patent teaches a single side only reflective optical inspection system.

The patent does not teach nor suggest an automated optical inspection system which provides simultaneous inspection of surface defects and drilled or etched holes in a product being inspected as it taught and claimed herein.

U.S. Pat. No. 5,268,735 teaches an optical inspection apparatus which can observe a light transmitted portion and a light reflected portion within objects of inspection distinguishable from each other within the same field of vision.

The patent does not teach nor suggest an automated optical inspection system which provides simultaneous inspection of surface defects and drilled or etched holes in a product being inspected as it taught and claimed herein.

U.S. Pat. No. 5,288,991 teaches an optical inspection system in which the surface of a substrate is scanned by a linear charge coupled device (CCD). The surface is illuminated in a narrowly focused strip from a broad band light source that is selectively wavelength filtered to optimize image contrast to the applicable characteristics of the surface under inspection.

The patent does not teach nor suggest an automated optical inspection system which provides simultaneous inspection of surface defects and drilled or etched holes in a product being inspected as it taught and claimed herein.

U.S. Pat. No. 5,301,012 teaches an optical technique for rapid inspection of via holes under etch and decontamination. The sensitivity and resolution of the automatic inspection system is enhanced by fully illuminating an area corresponding to a nominal-feature-shaped shape formed on a surface. Scanning of the illuminated area provides resolution of defects far smaller than the area of the illuminated spot. The patent employs a laser light source which provides for inspecting one surface of the product to be inspected.

The patent does not teach nor suggest an automated optical inspection system which provides simultaneous inspection of surface defects and drilled or etched holes in a product being inspected as it taught and claimed herein.

Although the prior art generally teaches optical inspection systems, the prior art does not teach an automated optical inspection system which allows for simultaneous reflective and thru-inspection of drilled or etched holes in a product being inspected.

SUMMARY OF THE INVENTION

It is an object of the present invention to improve automatic optical inspection of products having drilled or etched holes such that surface defects and defects in the holes of the product may be inspected by a dual mode illumination inspection system.

A dual mode illumination system for optical inspection of products for surface defects and defects in holes in the product includes a light source for providing illumination along an axis of one or more holes in the product to be inspected, the light source being positioned on a first side of the product, means for illuminating the surface of the second side of the product to be inspected, a beam splitter for redirecting light from the means for illuminating the second side of the product, to a light sensor while passing light from the light source to the light sensor. As an alternative, a second light source may be located adjacent to a second side of the product to be tested with the axis of illumination parallel to a major plane of the product. The light sensor may be a video camera connected to a data processing and display system It is an advantage of the present invention that inspection for defects in plated-through holes and drilled holes may be done simultaneously with inspection for surface defects on a printed circuit board or shadow mask or similar product.

The foregoing has outlined rather broadly the features and technical advantages of the present invention in order that the detailed description of the invention that follows may be better understood. Additional features and advantages of the invention will be described hereinafter which form the subject of the claims of the invention.

DETAILED DESCRIPTION OF PREFERRED EMBODIMENTS OF THE INVENTION

Automated optical inspection systems typically have one of two illumination configurations, one configuration being "reflective," for inspection of surface features of a product to be inspected, and the second illumination configuration being a backlit or through-lit configuration for the inspection of through-holes in the product being inspected. The combination of reflective and through-lit illumination for simultaneous use has been unknown prior to the present invention.

Apertures in a product to be inspected produced by a double-sided etching process create cross-sectioned aperture geometries which are trapezoidal in shape. That is, the walls of the hole are not perpendicular to the surface. For inspection of a product with such a trapezoidal shaped hole, it is desirable to detect manufacturing defects, both within the aperture, possibly on a side wall and on the flat outer surface between apertures.

Defects on the flat plane surface of the product can be imaged by using a reflective lighting system from the "front" or wide aperture side of the product. Defects on the side wall of the aperture or at the bottom, or narrow aperture side, of the product, resulting in a too wide aperture bottom, will not be reliably imaged from the top of the product using a reflective illumination system, since light shown into the aperture from the top will not reflect back into a light sensor such as a video camera directly over the product. A separate test must then be performed using either a through-light system to image the bottom opening of the hole or a reflective system positioned on the other side of the product (the "bottom" of the product) to image the bottom or narrow end of the aperture as a "dark" feature. Either method requires two separate optical inspections. A complete reflective imaging system could be installed on the "bottom" side of the product to be used simultaneously with a reflective imaging system placed on the "top" side of the product. However, this would double the number of cameras, thus greatly increasing the cost of the test fixture.

Figure 1:
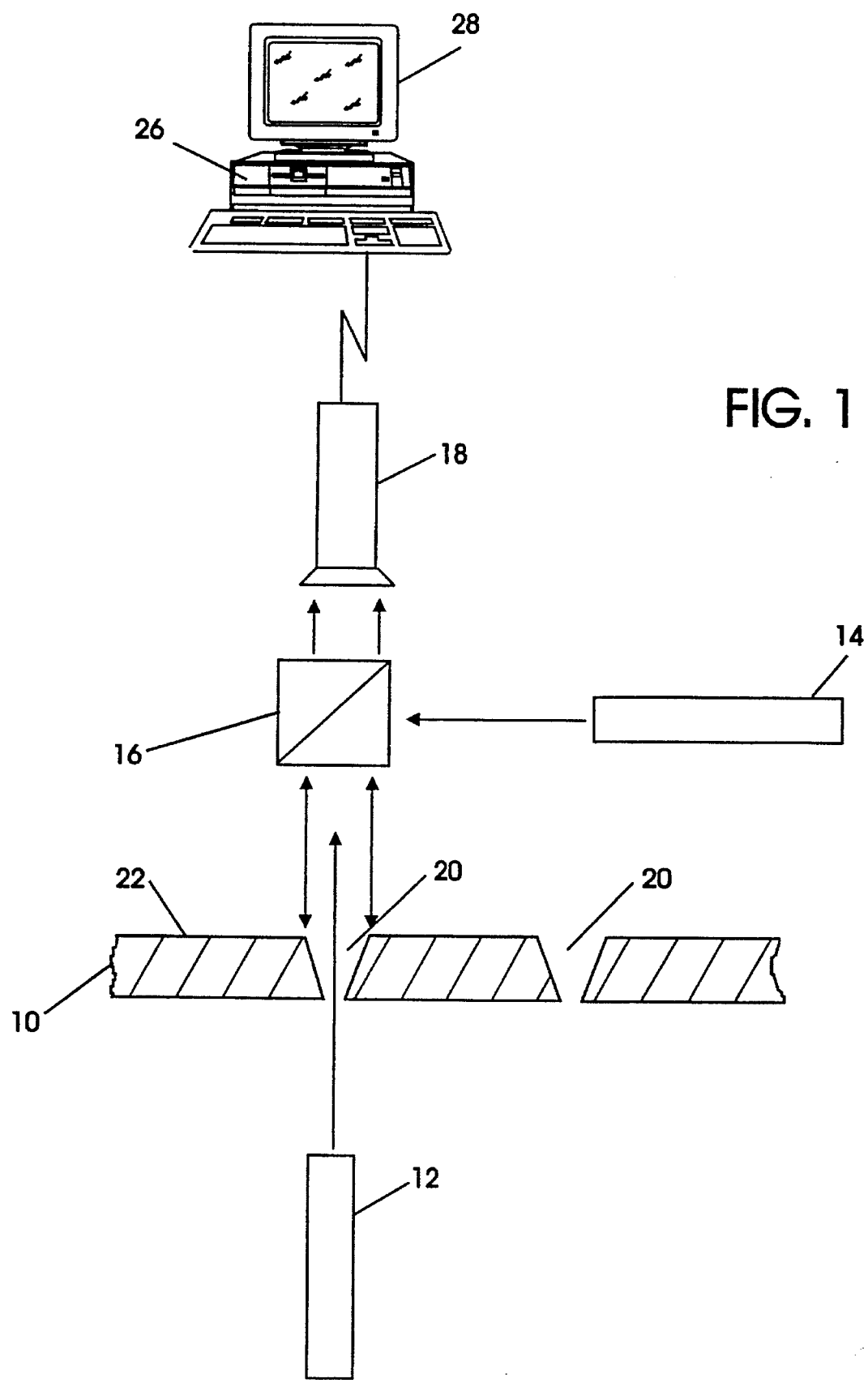
FIG. 1 is a schematic view of the automated optical inspection system in accordance with the present invention.

A solution to the problems posed by the prior art described above and in the Background of the Invention is to use a combination of reflective and through-lighting systems (See FIG. 1). Both aperture and surface plane geometries can be simultaneously imaged and defects subsequently detected in a single pass using a video camera positioned on the wide aperture side of the product. The through-lighting system will detect an "undercut" of the aperture as well as "back side" protrusions into the aperture. The trapezoidal cross-section of the aperture allows a reflective image and a through-light image to be taken simultaneously. An example of a product with apertures having trapezoidal shapes is a shadow mask for a cathode ray tube. Although other products having trapezoidal apertures therein, such as a printed circuit board, may be inspected by the system in accordance with the present invention, the preferred embodiment will be described with reference to imaging a cathode ray tube shadow mask.

Reflective illumination configurations typically consist of specular and diffuse components for the inspection of surface planes. Specular illumination creates a direct reflection from the plane surface to the light sensor. Diffuse or "odd angle" illumination creates reflection at differing angles which do not reflect directly into the light sensor but are useful for filling in uneven or granular surfaces in the product to be inspected.

Backlight or through-light illumination typically consists of a light source placed on one side of the product being inspected such that the light shines through open holes in the product to a light sensor placed on the opposite side of the product. It is very effective for imaging blocked or plugged holes in the product.

The angle of aperture walls of a product having trapezoidal shaped apertures therein is such that when the aperture is illuminated from above along the axis of the aperture, no light will reflect back into the light sensor placed directly above it.

An image taken using a reflective system would appear light in the surface area of the mask and dark in the aperture area including the aperture walls. The reflective system would also image defects such as pits, dents or scratches on the surface of the product between apertures. Such defects would image as dark regions in areas where there should only be light.

Referring now to FIG. 1, a preferred embodiment of the present invention will be described.

A panel 10 to be inspected such as a cathode ray tube shadow mask includes a number of trapezoid shaped apertures 20. As described above, a complete inspection requires a through-light and a reflective light to detect defects in apertures 20 as well as surface defects on panel 10.

Figure 5:
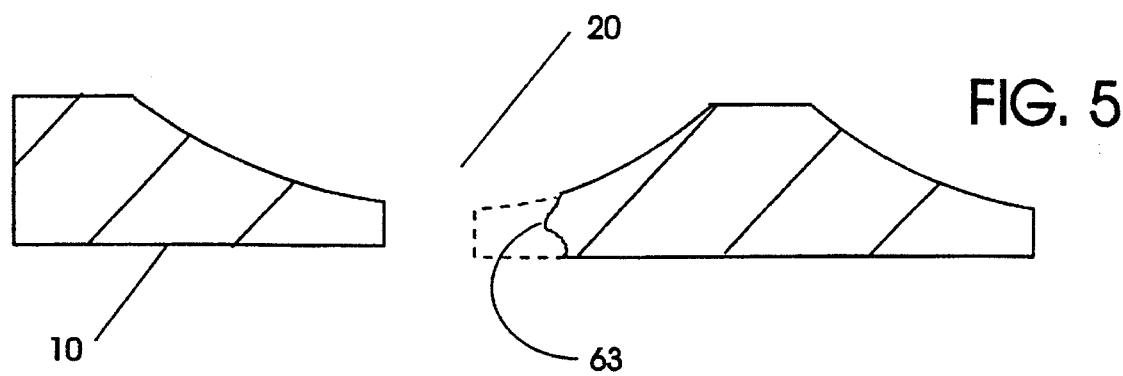
FIG. 5 is a cross-section view of a product to be inspected by the automated optical inspection system in accordance with the present invention showing a defect.
Figure 6:
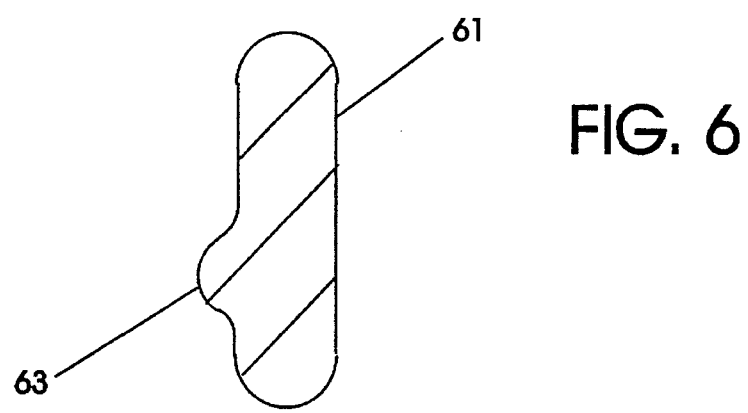
FIG. 6 is a backlit image of an aperture in a product showing a defect.

A backlight source 12 provides direct illumination of panel 10 from one side thereof, which will be referred to as the "back" or "bottom" of panel 10 herein. Backlight source 12 illuminates apertures 20 from a narrow end of the trapezoid shaped apertures 20 toward the wide end. The light from backlight source 12 then passes through beam splitter 16 and is detected by light sensor 18. Light sensor 18 may be implemented as a video camera which converts the light detected into an electronic image which is then processed by a data processing system, such as a personal computer (PC) 26 and viewed on a display device 28 attached to PC 26. Backlight source 12, beam splitter 16, and light sensor 18 are axially aligned along an axis perpendicular to the major plane of panel 10. Backlight source 12 detects defects in aperture 20 such as that shown in FIG. 5 and produces the image 61 in FIG. 6 showing, for example, the defect 63.

Figure 7:
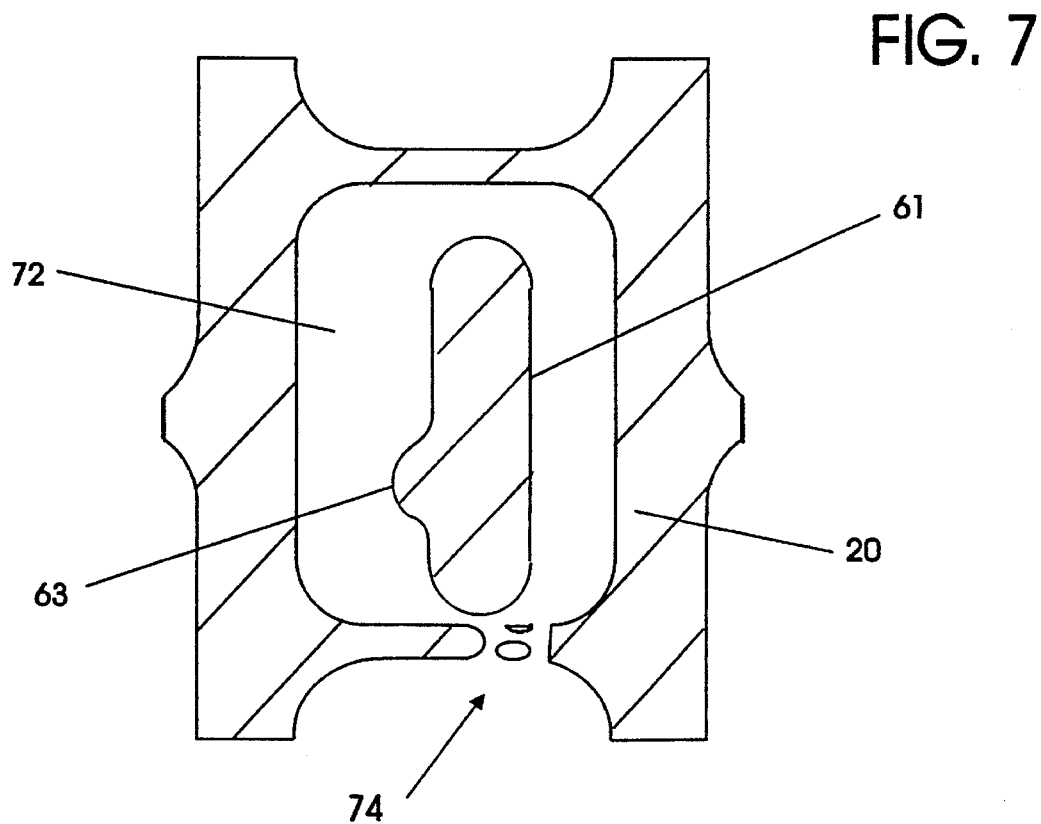
FIG. 7 is a composite image showing both reflective and backlit illumination of a product inspected by the automated optical inspection system in accordance with the present invention.

A second light source 14 is characterized as a reflective light source. Light from reflective light source 14 is directed through beam splitter 16 to a top surface 22 of panel 10. The incident light from reflective light source 14 is at 90 degrees to the axis of the light from backlight source 12 through beam splitter 16 to light sensor 18. The incident light from reflective light source 14 is reflected by beam splitter 16 along the backlight axis to the top surface 22 of panel 10. Light reflected from top surface 22 of panel 10 passes through beam splitter 16 along the axis which is 90 degrees to the major plane of panel 10 and is detected by light sensor 18 to form a composite image of both the backlight illumination and the reflective illumination. An example of the composite image is shown in FIG. 7 which combines the backlight image as described above with reference to FIG. 6 with the reflective image 72 of the aperture 20 where there is a defect 74 in aperture 20.

Figure 2:
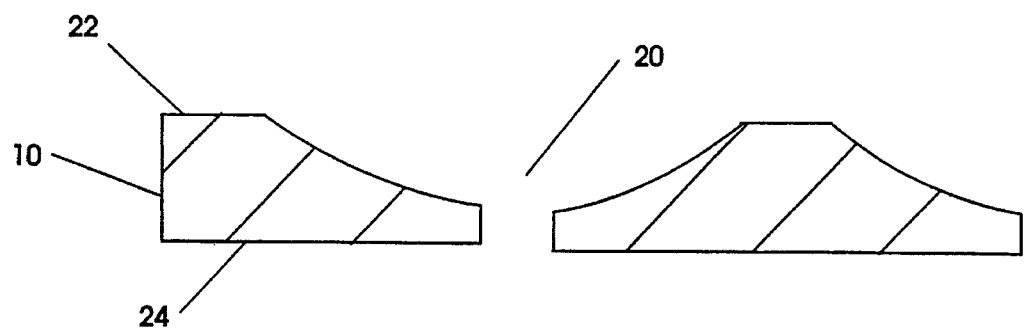
FIG. 2 is a partial cross-section view of a product including an aperture to be inspected by the automated optical inspection system according to the present invention.
Figure 3:
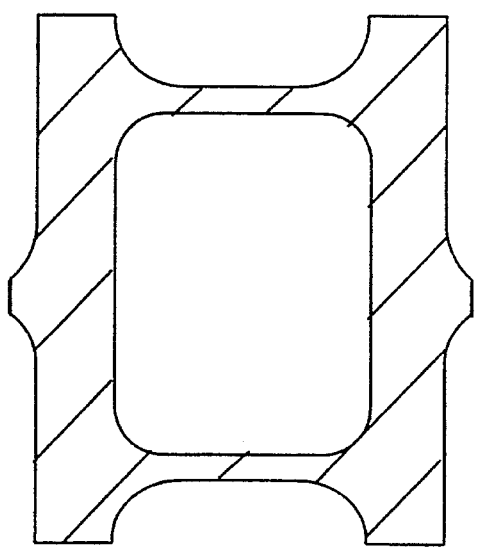
FIG. 3 is a reflective image of a surface without defect.
Figure 4:
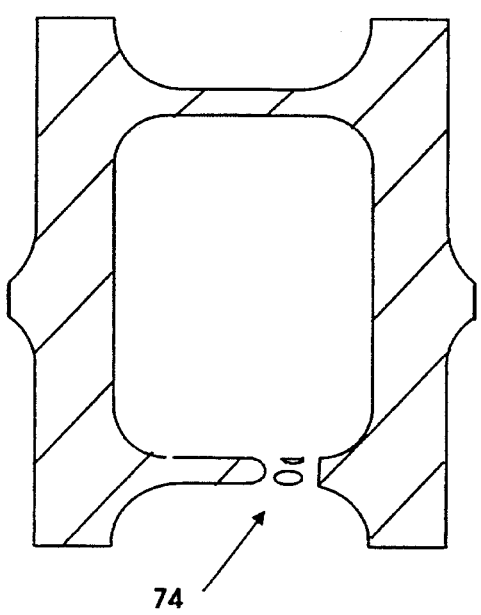
FIG. 4 is a reflective image of a surface showing a defect.

Referring now to FIGS. 2, 3, and 4, the images generated from the reflective light source will be further described. FIG. 2 is a cross-section view of panel 10 showing an aperture 20. Note the trapezoidal shape of aperture 20 where the aperture is much wider at surface 22 than at surface 24, the back side of panel 10. FIG. 3 is an example of a reflective image of the surface of panel 10. FIG. 4 is an example of a reflective image of the surface 22 of panel 10 showing a defect 74.

The illumination system in accordance with the present invention decreases the number of light sensors or separate tests required to properly show defects in products having trapezoid shaped apertures. By using both on axis reflective illumination and through-illumination simultaneously, a single composite image (see FIG. 7) can be taken using a light sensor such as a video camera to send to a test apparatus (not shown) including a video monitor (not shown) to detect defects.

Figure 8:
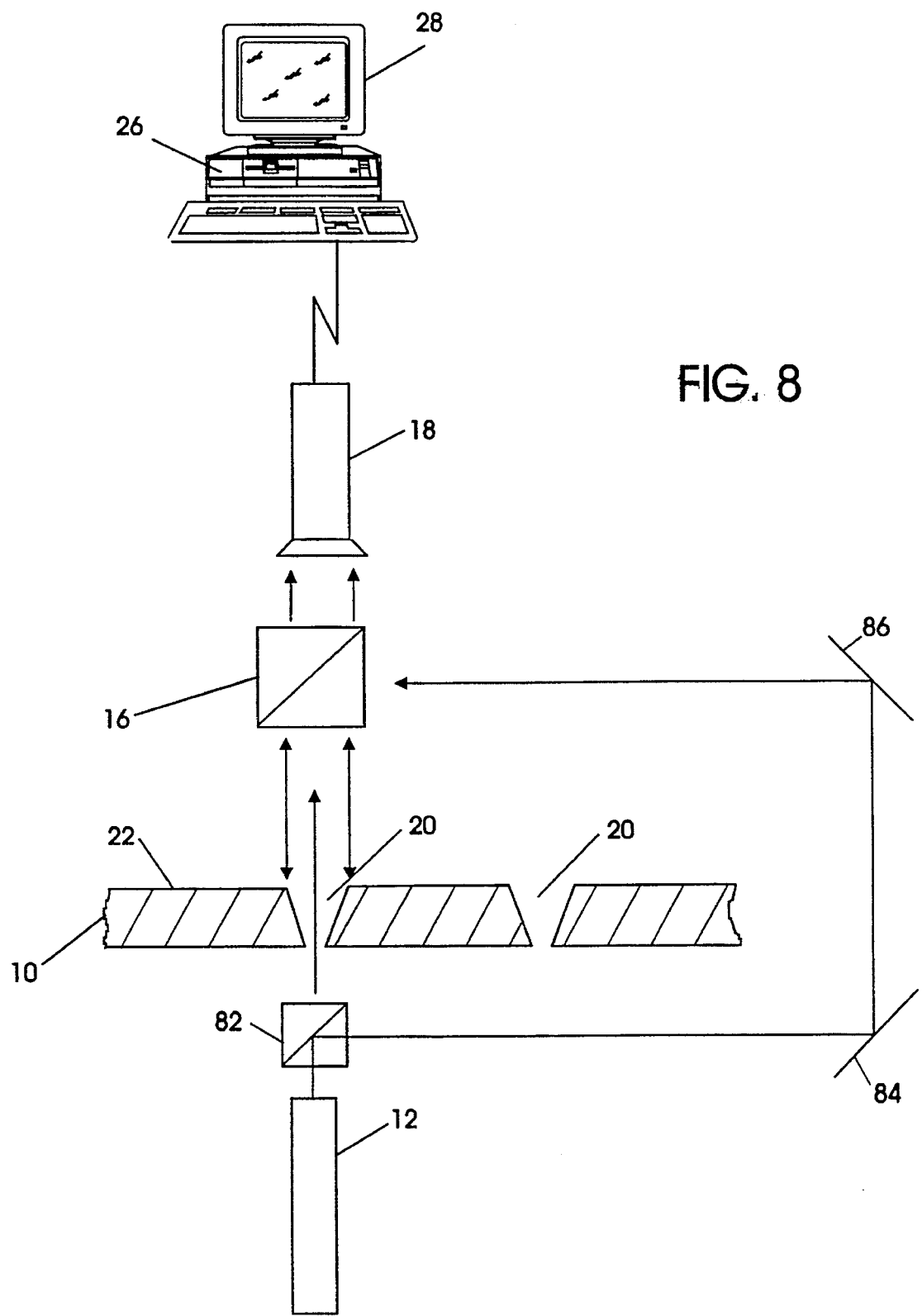
FIG. 8 is a schematic view of the automated optical inspection system in accordance with an alternate embodiment of the present invention.

In an alternate embodiment of the present invention, illustrated in FIG. 8, the second light source 14 (see FIG. 1) is eliminated and the top surface 22 of panel 10 is illuminated by light from light source 12, split by beam splitter 82 and reflected by mirrors 84 and 86. The alternate embodiment, is less expensive and reduces energy consumption by eliminating the second light source and the power to drive it.

The use of the images created by the system in accordance with the present invention are beyond the scope of this invention. Any of a number of known techniques may be employed with respect to the images created by the system in accordance with the present invention.

Although the present invention and its advantages have been described in detail, it should be understood that various changes, substitutions and alterations can be made herein without departing from the spirit and scope of the invention as defined by the appended claims.

What is claimed is:

1. An optical inspection system, comprising:
   a light source for illuminating a product under inspection from a first side thereof;
   means for illuminating a second side of and apertures in the product under inspection;
   a light sensor for receiving light carrying composite information related to the product under inspection; and
   a beam splitter for directing incident light from the means for illuminating to the second side of the product under inspection, and for passing light from the first light source carrying information related to the first side of the product and reflected light from the second side of the product to the light sensor.

2. An optical inspection system, according to claim 1, wherein the light sensor comprises a camera.

3. An optical inspection system, according to claim 2, wherein the light sensor comprises a video camera.

4. An optical inspection system, according to claim 1, wherein the light source and the light sensor are axially aligned with an axis of an aperture in the product.

5. An optical inspection system, according to claim 1, wherein the means for illuminating is an optical system, comprising:
   one or more reflective surfaces; and
   a beam splitter, axially aligned with the light source.

6. An optical inspection system, according to claim 1, wherein a first opening of the aperture on the first side of the product is less than a second opening of the aperture on the second side of the product, such that the aperture has a trapezoid cross section.

7. A method for optical inspection of a product having one or more apertures therein, comprising the steps of:
   first illuminating, with a light source, a first side of the product under inspection;
   second illuminating, with a means for illuminating, a second side of and apertures in the product under inspection;
   directing incident light, employing a beam splitter, from the means for illuminating, to the second side of the product under inspection;
   passing light from the light source carrying information related to the first side of the product and reflected light from the second side of the product to a light sensor; and
   receiving, in the light sensor, light carrying composite information related to the product under inspection; and
   displaying on a display device, a composite image of the product under inspection.

8. A method for optical inspection, according to claim 7, further comprising the step of:
   axially aligning the light source and the light sensor with an axis of an aperture in the product.

9. A method for optical inspection, according to claim 7, further comprising the step of:
   aligning the means for illuminating to provide illumination at an angle of ninety degrees to the axis of the aperture.

10. A method for optical inspection, according to claim 7, wherein a first opening of the aperture on the first side of the product is less than a second opening of the aperture on the second side of the product, such that the aperture has a trapezoid cross section.

11. An optical inspection system, comprising:
    a first light source for illuminating a product under inspection from a first side thereof;
    a second light source for illuminating a second side of and apertures in the product under inspection;
    a light sensor for receiving light carrying composite information related to the product under inspection; and
    a beam splitter for directing incident light from the second light source to the second side of the product under inspection, and for passing light from the first light source carrying information related to the first side of the product and reflected light from the second side of the product to the light sensor.

12. An optical inspection system, according to claim 11, wherein the second light source is aligned to provide illumination at an angle of ninety degrees to the axis of the aperture.

* * * * *